(12) United States Patent
Mickley et al.

(10) Patent No.: US 6,802,824 B2
(45) Date of Patent: Oct. 12, 2004

(54) CATHETER DEVICE AND METHOD FOR DELIVERING A DOSE INTERNALLY DURING MINIMALLY-INVASIVE SURGERY

(75) Inventors: Timothy J. Mickley, Elk River, MN (US); Bruce Arthur Christie, Upland, CA (US); Douglas F. Walker, Long Beach, CA (US); Jeremy L. Connell, Gladstone, OR (US)

(73) Assignee: SciMed Life Systems, Inc., Maple Grove, MN (US)

( * ) Notice: Subject to any disclaimer, the term of this patent is extended or adjusted under 35 U.S.C. 154(b) by 81 days.

(21) Appl. No.: 10/171,539

(22) Filed: Jun. 17, 2002

(65) Prior Publication Data

US 2003/0233076 A1 Dec. 18, 2003

(51) Int. Cl.[7] ............................................. A61M 5/178
(52) U.S. Cl. .................................. 604/164.12; 604/186
(58) Field of Search ........................... 604/158, 164.01, 604/164.12, 165.01, 246, 131, 134–136, 151, 156–157, 181, 187, 207–211, 186

(56) References Cited

U.S. PATENT DOCUMENTS

| 5,176,647 A | * | 1/1993 | Knoepfler ................... 604/158 |
| 5,336,172 A | * | 8/1994 | Bales et al. ................... 604/27 |
| 5,522,797 A | | 6/1996 | Grimm |
| 6,056,728 A | | 5/2000 | von Schuckmann |
| 6,183,444 B1 | | 2/2001 | Glines et al. |
| 6,641,566 B2 | * | 11/2003 | Douglas et al. ............. 604/218 |

FOREIGN PATENT DOCUMENTS

| WO | WO 96 16691 A | 6/1996 |
| WO | WO 01 87383 A | 11/2001 |

* cited by examiner

*Primary Examiner*—Loan H. Thanh
(74) *Attorney, Agent, or Firm*—Kenyon & Kenyon

(57) ABSTRACT

A catheter handpiece apparatus and method for delivering a desired dose with minimal potential for contamination of the injected substance and rapid, accurate delivery of the desired dose. In one embodiment, a carriage assembly affixed to an inner lumen is slidably located within a handpiece housing equipped with an outer lumen. The carriage assembly receives a dose carpule. An actuator knob cocks the carriage assembly and a spring-powered actuator mechanism. After the catheter is maneuvered to a desired injection site and a desired dose is set, depressing a first trigger causes the inner lumen tip to extend beyond the outer lumen into the injection site. Depressing a second trigger causes the actuator mechanism to push the desired dose from the dose carpule through the inner lumen into the injection site. A second embodiment provides a catheter handpiece with a carriage assembly cocking lever and an operator-powered dose delivery mechanism.

26 Claims, 8 Drawing Sheets

CATHETER DEVICE AND METHOD FOR DELIVERING A DOSE INTERNALLY DURING MINIMALLY-INVASIVE SURGERY

TECHNICAL FIELD

The present invention regards a catheter device and method for the delivery of medication to a desired location within a patient's body. More specifically, the present invention regards a device and method for reliable, simple and efficient delivery of a desired dose of medication to tissues within the body during minimally-invasive surgery procedures whereby a catheter handpiece is configured for deployment of a needle by the pressing of a single trigger and delivery of a desired dose of medication by pressing of another trigger.

BACKGROUND

The deployment in the body of medication and other substances, such as materials useful in tracking biological processes through non-invasive imaging techniques, is an often repeated and advantageous procedure performed during the practice of modern medicine. Such substances may be deployed in either case through non-invasive procedures such as endoscopy and through more invasive procedures that require larger incisions into the body of a patient. The non-invasive and less-invasive procedures are generally used when the target area is accessible through a lumen of the body, while the more invasive procedures may be employed when the target area is located deep within the body or otherwise not readily accessible through a lumen of the body.

Previously, injection of medication in minimally-invasive procedures required, among other complications, careful, time-consuming manual monitoring of the placement of the catheter tip within the body and the amount of medication or other substance being delivered during the injection procedure, potential exposure of the medication and other substances to the atmosphere during the handling of containers in preparation for dose injection, and, in the case of injection of multiple medications or other substances, time-consuming work to either remove and replace the catheter dose injection equipment or to prepare the equipment for re-use.

SUMMARY OF THE INVENTION

The present invention is directed to addressed the foregoing concerns with previous catheter injection systems. In one embodiment of the present invention, there is provided a drug delivery device for delivering a desired dose to an injection site within a patient's body. The device includes a catheter handpiece, wherein the catheter handpiece has an outer handpiece body and an inner carriage assembly, and the inner carriage assembly can slide between a lumen end and an opposing actuator end of the handpiece body. The carriage assembly is biased toward the lumen end of the handpiece body by a spring. The handpiece body has an aperture through which a dose carpule is inserted to rest in the carriage assembly. An outer lumen is affixed to the lumen end of the handpiece body, and an inner lumen is affixed to the lumen end of the carriage assembly, such that when the carriage assembly slides toward the lumen end of the handpiece body, the inner lumen slides within the outer lumen a sufficient distance for the distal end of the inner lumen to extend beyond the distal end of the outer lumen, exposing an injection needle tip.

At the lumen end of the carriage assembly there is a dose carpule receiving flange. The proximal end of the inner lumen is affixed to the lumen end of the dose carpule receiving flange, which is configured to receive the dose carpule and guide the desired dose from the dose carpule into the inner lumen when a dose delivery actuator at the actuator end of the carriage assembly causes a dose delivery actuator to push on a piston within the dose carpule. Adjacent to the lumen end of the dose actuator is a dose carpule pressing block which presses the dose carpule toward the dose carpule receiving flange when an aperture door covering the handpiece body aperture is closed.

The catheter handpiece is prepared for use by actuation of an actuator cocking member located at the actuator end of the handpiece body. In this embodiment, the actuator cocking member is a knob which rotates about an axis parallel to the longitudinal axis of the carriage assembly. When the actuator cocking member is rotated by an operator, the carriage assembly is pulled toward the actuator end of the handpiece body until captured by the carriage release trigger, and a dose delivery actuator tube is rotated until captured by the dose release trigger. During the movement of the carriage assembly and the dose delivery actuator tube, the dose delivery actuator rod is prevented from being retracted by a ratchet mechanism. Once the catheter is located at the desired injection site within the patient's body, the carriage release trigger may be actuated, whereupon the carriage assembly is released from its cocked position and slides toward the lumen end of the body, thereby extending the distal end of the inner lumen beyond the distal end of the outer lumen and causing the attached injection needle to penetrate the tissue at the desired injection site. Following deployment of the inner lumen, the dose release trigger may be actuated, whereupon the dose delivery actuator is released from its cocked position and a spring causes the dose actuator tube to rotate, which advances the actuator rod by means of a threaded dose delivery actuator nut through which the actuator rod passes toward the actuator end of the dose carpule. The actuator rod thus applies a force to the carpule piston to cause the desired dose to be delivered from the dose carpule through the dose carpule receiving flange and the inner lumen to the desired injection site. The amount of dose delivered is controlled by a dose metering member, which limits the motion of the dose delivery actuator tube, nut and rod, and thereby limits amount of medication discharged from the dose carpule. Following injection of the desired dose, the catheter handpiece may be cocked, withdrawing the inner lumen and injection needle back within the outer lumen. The catheter then may be repositioned to another desired injection location within the patient's body for delivery of an additional dose from the installed dose carpule in the manner described above. The dose delivery process may be repeated until the desired number of doses have been delivered from the carpule, or the carpule is spent, whichever occurs first. When no further doses are to be delivered from the dose carpule, the catheter handpiece may be cocked to withdraw the inner lumen tip into the outer lumen prior to removal of the catheter from the patient's body.

In a second embodiment of the present invention, the actuator is not powered by a spring, but instead the actuator rod moves toward the catheter end of the carriage assembly, thereby contacting and advancing the dose carpule piston, by manual turning of the actuator advancing knob at the actuator end of the handpiece body. Cocking of the needle release mechanism is accomplished by manual squeezing and pivoting of a cocking lever.

The present invention further includes a method for delivering the desired dose to a desired injection location. The method includes: (a) inserting a dose carpule through an aperture in the catheter handpiece affixed to the catheter into the carriage assembly and closing the aperture door in order to urge the dose carpule toward a receiving flange on the carriage assembly; (b) priming the inner lumen to remove air therein by setting a desired dose setting on a dose metering member in the handpiece body, rotating the actuator cocking knob on the end of the catheter handpiece opposite the catheter until the carriage assembly and the dose delivery actuator are in their respective cocked positions, depressing the carriage release trigger to cause the carriage assembly to slide toward the lumen end of the catheter handpiece, and depressing the dose release trigger to cause the dose actuator rod to apply a force to the dose carpule to cause the substance to be injected therein to pass from the dose carpule through the dose receiving flange and though the inner lumen and reach the end of the injection needle tip (this sequence is repeated until the medication reaches the injection needle tip); (c) rotating the actuator cocking knob on the end of the catheter handpiece opposite the catheter until the carriage assembly and the dose delivery actuator are in their respective cocked positions; (d) inserting the catheter including an outer lumen and an inner lumen into a patient's body and maneuvering the catheter to a desired dose injection site; (e) depressing the carriage release trigger to cause the carriage assembly to slide toward the lumen end of the catheter handpiece and thereby cause the inner lumen affixed to the carriage assembly to extend beyond the distal end of the outer lumen into the desired injection site; and (f) depressing the dose release trigger to cause the dose actuator rod to apply a force to the dose carpule to cause the desired dose to pass from the dose carpule through the dose receiving flange, though the inner lumen and its injection needle tip and be deposited at the desired injection site. Alternatively, instead of depressing a dose release trigger, when using a non-spring powered embodiment of the present invention, the operator may advance the dose actuator rod toward the dose carpule by manually rotating the actuator advancing knob. Following dose delivery, the catheter handpiece may be cocked, withdrawing the inner lumen and injection needle back within the outer lumen. The catheter then may be repositioned to another desired injection location within the patient's body for delivery of an additional dose by resetting the desired dose, depressing the needle release trigger, and depressing the dose release trigger or, in the second embodiment, turning the actuator advancing knob in the manner described above. The dose delivery process may be repeated until the desired number of doses have been delivered from the carpule or the carpule is spent, whichever occurs first, at which point the catheter handpiece may be cocked to withdraw the inner lumen tip into the outer lumen prior to removal of the catheter from the patient's body.

DETAILED DESCRIPTION

First Embodiment

Figure 1:
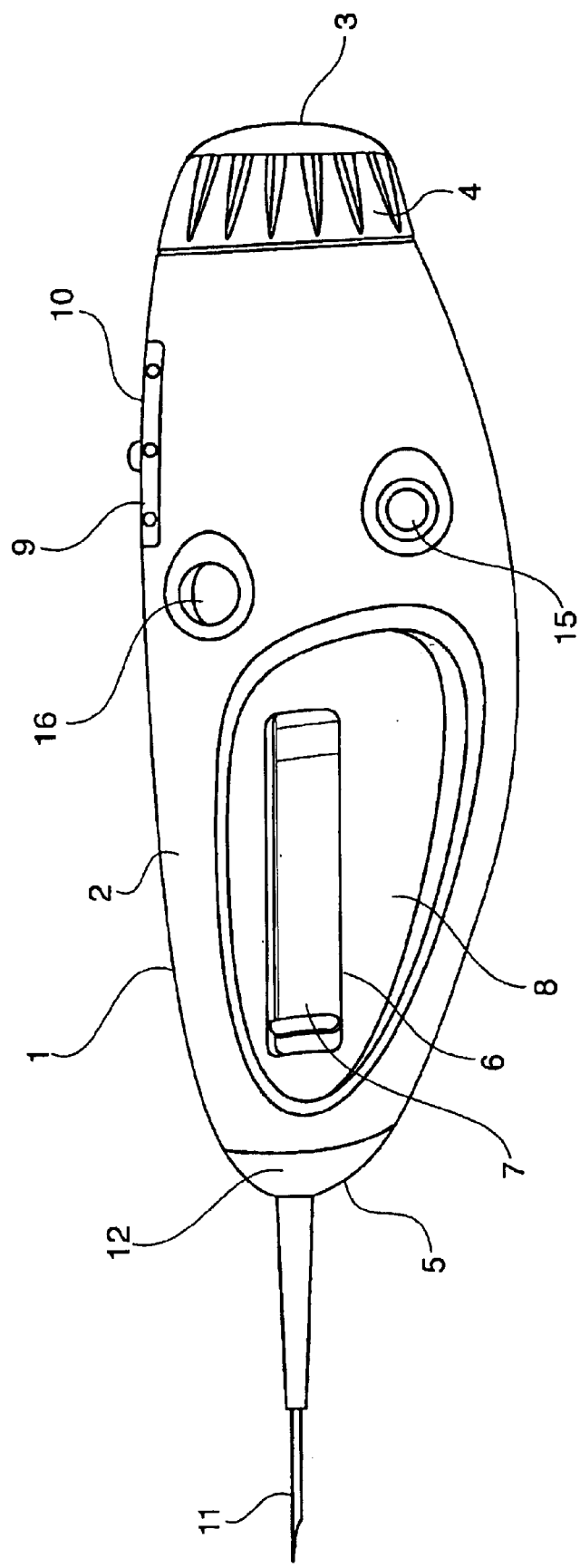
FIG. 1 is a side view of a catheter handpiece in accordance with a first embodiment of the present invention.

FIG. 1 is a side view of a catheter handpiece 1 of a first embodiment of the present invention. The handpiece housing 2 in this embodiment may be made from any biocompatible and sufficiently rigid material including plastic and hard rubber. As shown in FIG. 1, catheter handpiece 1 has at its actuator end 3 an actuator knob 4 for cocking the catheter handpiece. Toward catheter handpiece lumen end 5, there is a dose carpule insertion aperture 6 with an aperture door 7. In this embodiment, there is also provided near dose carpule insertion aperture 6 a rubber grip surface 8 to enhance operator control of the handpiece. Toward actuator end 3 of the catheter handpiece there is a dose metering member 9 which is used to set the amount of dose desired to be injected into the patient when the catheter handpiece is activated. Next to dose metering member 9 is a replaceable dose metering label 10 to provide the operator with an indication of the amount of dose that will be injected at various settings of dose metering member 9. Dose metering label 10 may be replaced as necessary to ensure the dose selected with dose metering member 9 corresponds to the dose delivered by the particular dose carpule being used.

Figure 2:
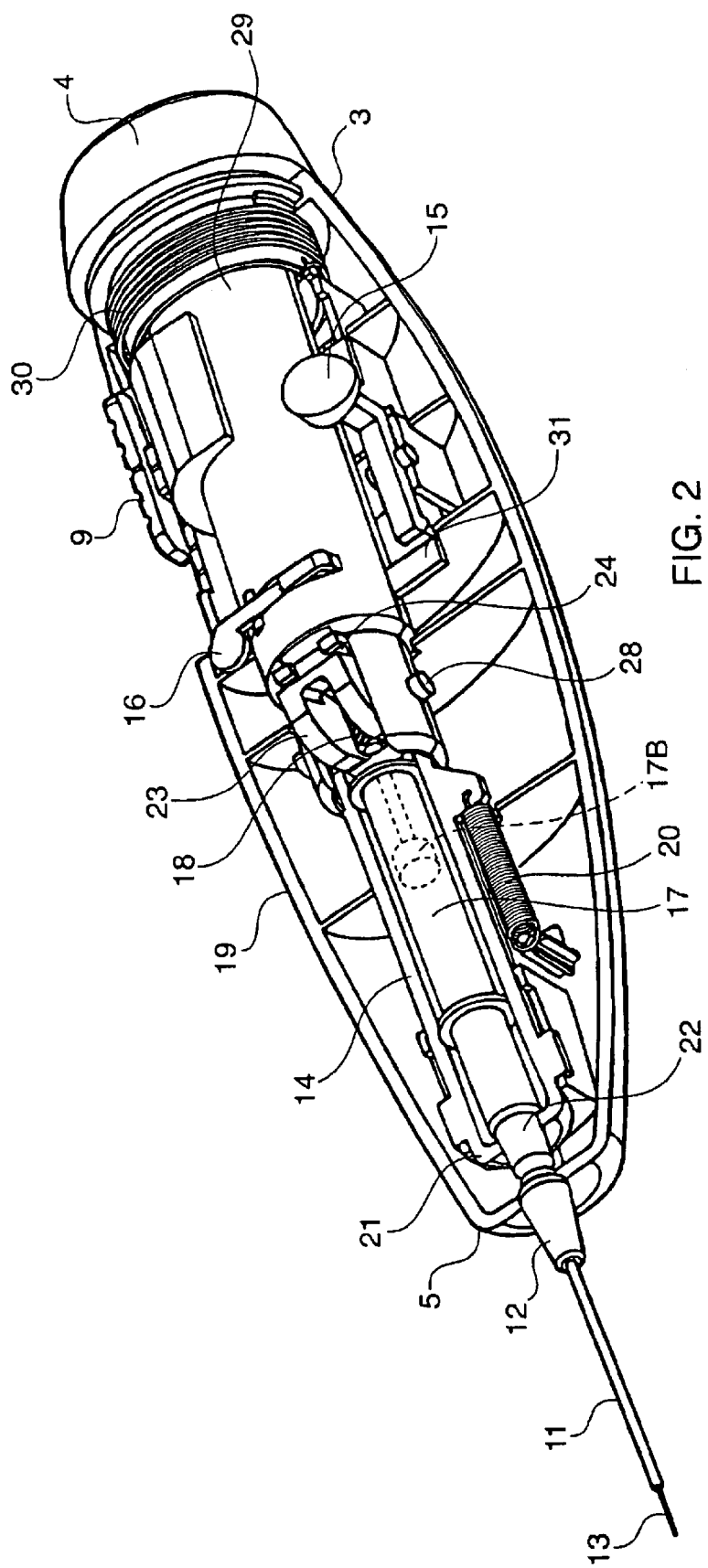
FIG. 2 is a view of the internal arrangement of a lower portion of the catheter handpiece housing and the carriage assembly in accordance with a first embodiment of the present invention.

FIG. 1 further shows a catheter affixed at its proximal end to the lumen end 5 of the handpiece, comprising an outer lumen 11 and a strain relief member 12. An inner lumen resides within outer lumen 11, and is affixed at its proximal end to a carriage assembly slidably located within handpiece housing 2 (inner lumen 13 and carriage assembly 14 are shown in FIG. 2 and discussed further, below). The catheter is inserted into a patient's body and maneuvered to the desired injection site using techniques well known to practitioners. Once properly positioned, a carriage assembly release trigger 15 releases carriage assembly 14, which slides toward lumen end 5 of catheter handpiece 1 and thereby extends the distal end of inner lumen 13 and an injection needle tip at the end thereof (not shown) beyond the distal end of outer lumen 11 and into tissue at the desired dose injection site. Catheter handpiece 1 also contains a dose delivery actuator trigger 16, which releases a dose delivery actuator within the carriage assembly to permit a dose delivery actuator rod to apply a force to a dose carpule 17 (specifically, to carpule piston 17B), thereby causing the desired dose to pass from the dose carpule through inner lumen 13 to the desired injection site (dose delivery actuator 18 and dose carpule 17 are shown in FIG. 2).

FIG. 2 is a view of the internal arrangement of a portion of the catheter handpiece housing 1 and carriage assembly 14 in accordance with a first embodiment of the present invention. As shown in FIG. 2, carriage assembly 14 is slidably located within handpiece housing member 19 such that carriage assembly 14 can slide between lumen end 5 and actuator end 3 of the catheter handpiece housing. A spring 20 is connected at one end to carriage assembly 14 and at its other end to handpiece housing member 19, and biases carriage assembly 14 toward lumen end 5 of the catheter handpiece housing. At the carriage assembly's lumen end 21 there is a dose carpule receiving flange 22, to which the proximal end of inner lumen 13 is affixed. As in FIG. 1, outer lumen 11 is shown affixed via strain relief member 12 to lumen end 5 of handpiece housing member 19.

Figure 3:
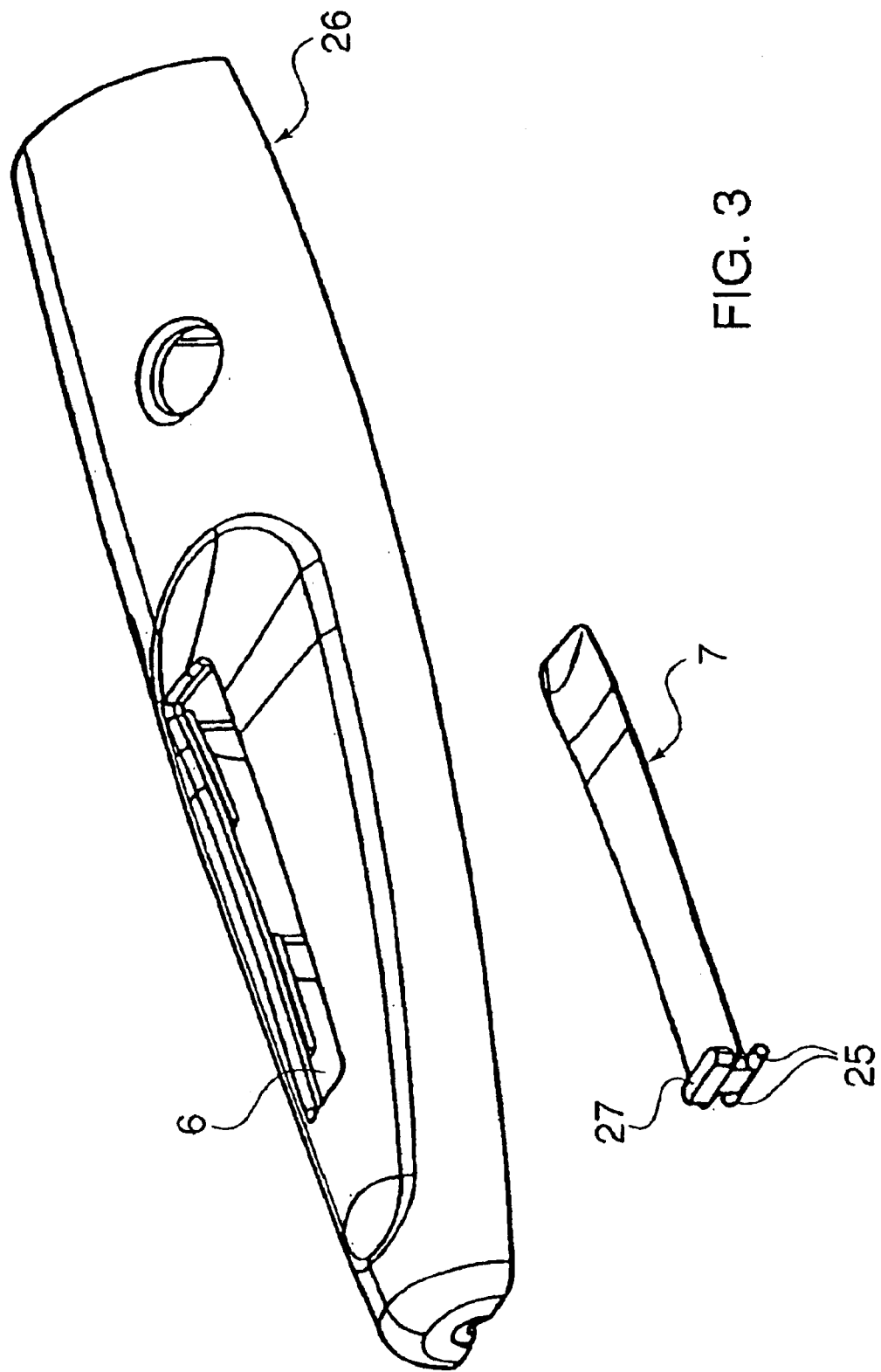
FIG. 3 is a view of an upper portion of the catheter handpiece housing and the dose carpule insertion aperture door in accordance with a first embodiment of the present invention.
Figure 4:
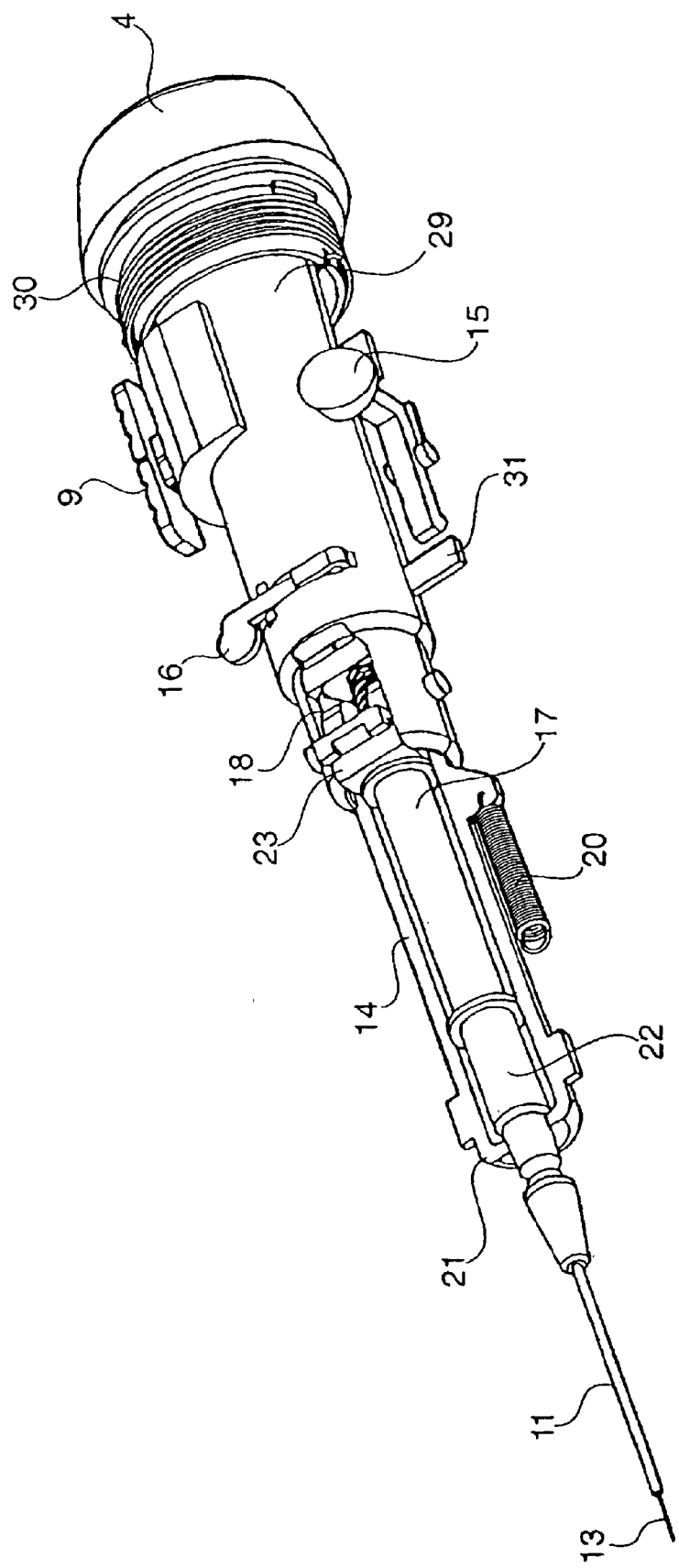
FIG. 4 is a view of the carriage assembly in accordance with a first embodiment of the present invention.

The face of dose carpule receiving flange 22 opposite inner lumen 13 is tapered to receive a mating tapered protrusion (not shown) at the front of dose carpule 17 when the carpule is inserted into carriage assembly 14. Once in the carriage assembly, dose carpule 17 is urged into mating contact with dose carpule receiving flange 22 by dose carpule pressing block 23. Referring now to FIGS. 2 and 3, dose carpule pressing block 23 has grooves 24 which engage corresponding engagement pins 25 on handpiece housing aperture door 7, which is slidably located within a second handpiece housing member 26 such that aperture door 7 may slide beneath aperture 6 between open and closed positions by applying pressure on door operating tab 27. As aperture door 7 is moved from the open position to the closed position, door pins 25 engaged in dose carpule pressing block grooves 24 cause dose carpule pressing block 23 to pivot on carriage assembly 14 about pivot pins 28. Pressing block 23 thus rotates toward, and begins pressing against, the end of dose carpule 17. This motion in turn urges dose carpule 17 into mating contact with dose carpule receiving flange 22 with a locking cam action. As aperture door 7 continues toward the closed position, door pins 25 disengage from dose carpule pressing block grooves 24. In FIG. 2, dose carpule pressing block 23 is shown in its disengaged position. In FIG. 4, dose carpule pressing block 23 is shown in its fully engaged position, pressing dose carpule 17 into mating contact with dose carpule receiving flange 22.

Referring again to FIG. 2, located between dose carpule 17 and actuator end 29 of the carriage assembly is dose delivery actuator rod 18, the operating mechanism for which will be described further, below. Dose delivery actuator rod 18 is positioned on carriage assembly 14 such that when actuated, the actuator moves toward dose carpule 17, through dose carpule pressing block 23, and applies a force to dose carpule piston 17B that causes the medication in dose carpule 17 to pass from the carpule through dose carpule receiving flange 22 and inner lumen 13, into the desired injection site within the patient's body.

Also shown in FIG. 2 is actuator knob 4 at actuator end 3 of handpiece housing member 19. Actuator knob 4 is located by a flange adjacent to the end of housing member 19, such that the knob may be rotated about an axis parallel to a longitudinal axis of carriage assembly 14. Actuator knob 4 has around its outer periphery a spring 30 attached at one end to actuator knob 4 and at its other end to handpiece housing member 19, such that spring 30 returns actuator knob 4 to a rest position following the knob's use to cock the catheter handpiece prior to dose delivery. The inner diameter of actuator knob 4 is sufficiently large to surround the actuator end 29 of carriage assembly 14.

Additional features shown in FIG. 2 include dose metering member 9, which in this embodiment is captured between the two catheter handpiece housing members 19 and 26 during assembly of the housing. Dose metering member 9 is configured such that its inner surface cooperates with the carriage assembly's actuator mechanism to limit the travel of the dose delivery actuator, and thus dose delivery actuator rod 18, thereby limiting the dose delivered from dose carpule 17 to the injection site dose. Specifically, the inner surface of dose metering member 9 has a graduated stepped surface which, in combination with a dose stop tab on the dose delivery actuator mechanism, limits dose delivery to specific, discrete quantities.

Also shown in FIG. 2 are carriage release trigger 15 and carriage assembly cocking tab 31. Upon cocking catheter handpiece 1, carriage assembly 14 slides toward the actuator end of handpiece housing 19 until a carriage assembly cocking tab 31 is caught and releasably held by carriage release trigger 15.

Figure 5:
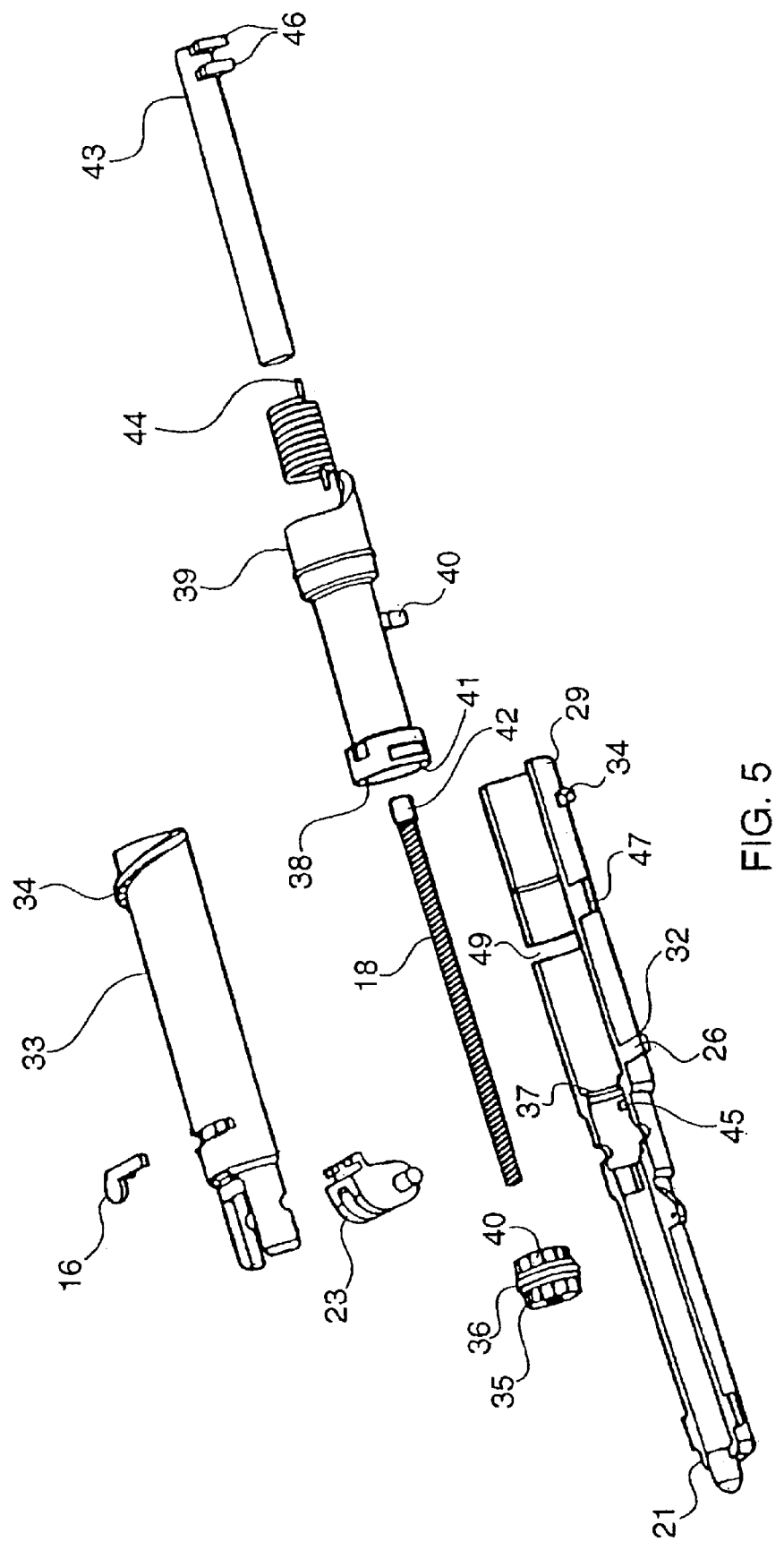
FIG. 5 is an exploded view of the carriage assembly showing components which cooperate with the dose delivery actuator to permit its operation in accordance with a first embodiment of the present invention.

FIG. 5 shows an exploded view of carriage assembly actuator mechanism. Carriage assembly 14 has a lower member 32 and upper member 33 between which the components of the dose delivery actuator mechanism reside. On the outside of carriage assembly members 32 and 33, adjacent to actuator end 29, is a stepped helical ridge 34. Helical ridge 34 cooperates with a corresponding tab within the inner diameter of actuator knob 4 (not shown) such that as actuator knob 4 is rotated, the tab within the knob slides along ridge 34, pulling carriage assembly 14 toward the actuator end 3 of catheter handpiece 1 until dose carriage cocking tab 31 is captured by carriage assembly release trigger 15.

The following describes the arrangement and operation of the dose delivery actuator in the first embodiment of the present invention. Dose delivery actuator rod 18 in this embodiment has external threads along its length which engage corresponding internal threads in a hole in the center of dose delivery actuator nut 35. Actuator nut 35 also has a circumferential groove 36 that rests against indexing surfaces 37 in the interior of carriage assembly members 32 and 33 (indexing surface within member 33 not shown) and the face 38 of actuator tube 39, such that actuator nut 35 is constrained from moving toward the lumen end 21 or actuator end 29 of the carriage assembly. As a result of this arrangement, actuator nut 35 may only rotate about the longitudinal axis of dose delivery actuator rod 18. Due to the interaction between the threads on dose delivery actuator rod 18 and the threads in actuator nut 35, when actuator nut 35 rotates about dose delivery actuator rod 18, the actuator rod moves toward lumen end 21.

Actuator nut 35 further has ratchet teeth 40 formed on both sides of its outer circumference adjacent to circumferential groove 36. Actuator nut ratchet teeth 40 are releasably engaged, on one side of circumferential groove 36 by the engagement of a ratchet pawl 45 on carriage assembly member 33, and on the other side of the nut by corresponding ratchet hooks 41 within the face of lumen end of actuator tube 39. The actuator nut ratchet teeth 40 on both sides of circumferential groove 36 are arranged in same direction, such that when ratchet pawl 45 is engaged with one row of teeth 40, actuator nut 35 cannot rotate in a clockwise direction viewed from the lumen end of the carriage assembly.

Dose delivery actuator rod 18 has at its actuator end a square-head 42 which engages a corresponding recess within substantially the entire length of dose delivery actuator drive nut 43. Actuator drive nut 43 in turn rests concentrically within dose delivery actuator spring 44 and dose delivery actuator tube 39. One end of actuator spring 44 engages holes in tabs 46 on the end of actuator drive nut 43, while the other end of the spring engages a hole on an interior surface within actuator tube 39, such that when actuator tube 39 is turned relative to actuator drive nut 43, energy is stored in actuator spring 44. Engagement tabs 46 at the end of actuator drive nut 43 also serve to engage actuator drive nut slot 47 in carriage assembly lower member 32, such that dose drive nut 43 cannot rotate relative to carriage assembly 14.

The dose delivery actuator is cocked by turning actuator knob 4, which is internally configured to simultaneously cooperate with the end of actuator tube 39 and carriage assembly 14. As actuator knob 4 is turned counter-clockwise viewed from the lumen end of carriage assembly 14, the carriage assembly is drawn toward the actuator end of catheter handpiece housing 1 and releasably held by carriage assembly release trigger 15 in the manner previously described. Simultaneously, the counter-clockwise rotation of actuator knob 4 rotates actuator tube 39, causing ratchet teeth 41 on the face of actuator tube 39 to ratchet over ratchet teeth 40 on actuator nut 35, storing energy in spring 44, while also permitting dose delivery actuator trigger 16 to capture actuator tube 39 in its cocked position. Actuator nut 35 is prevented from rotating with actuator tube 39 by the engagement of ratchet pawl 45 on carriage assembly member 33 with the distal teeth of actuator nut 35. The pitch of the internal and external threads of actuator nut 35 and dose delivery actuator rod 18 are selected to achieve the desired range of axial motion of dose delivery actuator rod 18 within a relatively short arc of actuator tube 39 rotation when the stored energy in spring 44 is released by activating dose release trigger 16.

Upon reaching the fully cocked position, release of actuator knob 4 by the operator will result in actuator knob biasing spring 30 rotating the knob clockwise back to its rest position. After the cocking of the catheter handpiece and before triggering dose delivery, the desired dose setting may be set by sliding dose metering member 9 to the appropriate dose setting as indicated on dose label 10.

The following describes the operation of the dose delivery actuator to deliver the desired dose after the actuator mechanism is cocked in the manner described above. Following release of carriage assembly 14 from its cocked position by depression of carriage release trigger 15, an operator may depress dose delivery trigger 16 to cause the desired dose to be delivered. Depression of dose delivery trigger 16 causes its hook end to pivot clear of actuator tube 39. Due to the energy stored in actuator spring 44, actuator tube 39 and actuator nut 35 (which are engaged by ratchet teeth 40 and 41) begin to rotate clockwise. The clockwise rotation of actuator nut 35 drives dose delivery actuator rod 18 toward, and into contact with, carpule piston 17B, forcing at least a portion of the contents of the carpule into dose carpule receiving flange 22 and thence through inner lumen 13 to the desired injection site. The clockwise rotation of actuator nut 35 and axial motion of dose delivery actuator rod 18 continue until dose metering stop tab 40 reaches the step on inner surface of dose metering member 9 corresponding to the desired dose. When dose metering stop tab 40 reaches the selected dose stop step, the clockwise rotation of actuator tube 39 and actuator nut 35 and the axial motion of dose delivery actuator rod 18 toward the lumen end of carriage assembly 14 are halted, completing the delivery of the desired dose.

Associated with the foregoing embodiment of the present invention is a method for delivery of a desired dose using a catheter handpiece of significantly simplified operation. In preparation for delivery of a desired dose of medication or other substance, such as an imaging agent, to a desired injection site within a patient's body, the catheter handpiece of the first embodiment may be prepared for use by placing a dose carpule containing the substance to be injected into the patient through carpule insertion aperture 6 and into carriage assembly 14, and then closing aperture door 7 to cause the dose carpule to be urged into mating contact with dose carpule receiving flange 22. At this time, adhesive dose metering label 10 may be affixed to the catheter handpiece body adjacent to dose metering member 9 to guide the setting of the desired dose to be injected, and dose metering member 9 may be set to the desired dose.

Next, the catheter handpiece operator cocks the catheter handpiece by gripping the handpiece in one hand and using the other hand to rotating actuator knob 4 clockwise viewed from the actuator knob end of the handpiece until the dose actuator mechanism in carriage assembly 14 reaches the end of its travel and actuator knob 4 stops. Upon release of actuator knob 4 by the operator, the knob rotates counter-clockwise back to its starting position.

Next, the operator depresses carriage assembly release trigger 15 and dose delivery trigger 16 to prime the inner lumen with the substance to be injected. The cocking and firing sequence may be repeated until the substance to be injected has reached the distal end of inner lumen 13. Once primed, the catheter handpiece may be re-cocked in the manner previously described and the physician may insert the catheter, comprising outer lumen 11 and inner lumen 13, into the patient's body and maneuver the catheter to the desired injection site in the conventional manner.

Once the catheter is located at the desired injection site, the catheter operator may depress carriage assembly release trigger 15 to cause carriage assembly 14 to slide forward and thus cause the distal end of inner lumen 13 to extend beyond outer lumen 11 into the desired injection site. Once inner lumen 13 has been deployed at the desired injection site, the catheter operator may depress dose delivery trigger 16, thereby permitting dose delivery actuator rod 18 to press on the dose carpule piston 17B and thereby cause the desired dose to pass from the dose carpule through dose carpule receiving flange 22 and into inner lumen 13, and thence into the desired injection site. Following delivery of the desired dose, the catheter handpiece may be cocked, withdrawing the inner lumen and injection needle back within the outer lumen. The catheter then may be repositioned to another desired injection location within the patient's body for delivery of an additional dose in the manner described above. The dose delivery process may be repeated until the desired number of doses have been delivered from the carpule or the carpule is spent, whichever occurs first, at which point the catheter may be removed from the patient's body.

Second Embodiment

The second embodiment of the present invention shares the majority of the principal features of the first embodiment, with differences in detail principally due to the second embodiment's dose delivery actuator being deployed manually by the operator, rather than, as in the first embodiment, by utilizing stored spring energy to deploy the dose delivery actuator.

Figure 6:
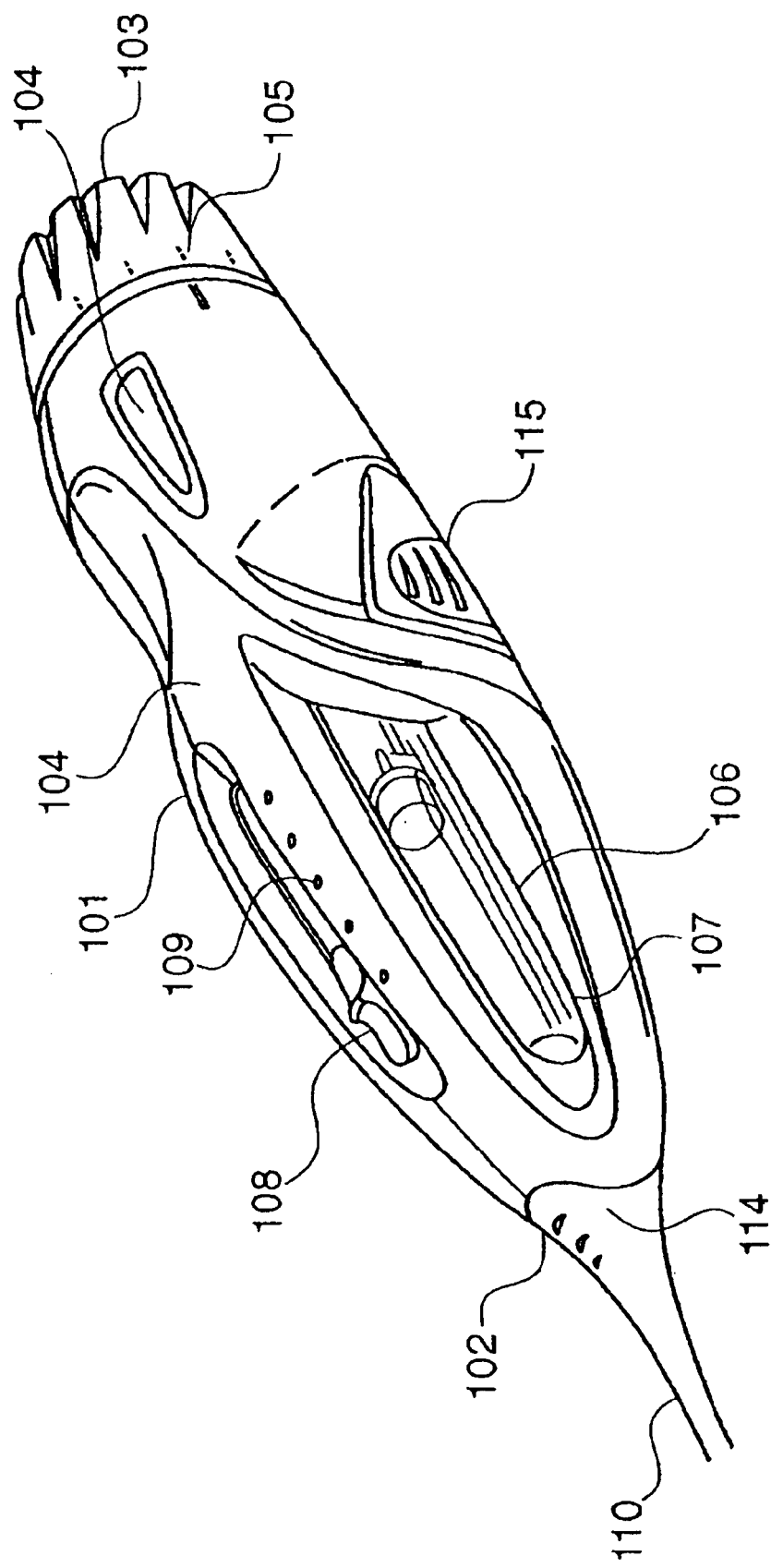
FIG. 6 is an oblique view of a catheter handpiece in accordance with a second embodiment of the present invention.

FIG. 6 is an oblique view of a catheter handpiece in accordance with a second embodiment of the present invention, showing catheter handpiece 101, with a lumen end 102 and an actuator end 103. As in the first embodiment, handpiece housing 104 may be made from any biocompatible and sufficiently rigid material including plastic and hard rubber. At its actuator end 103, catheter handpiece 101 has an actuator knob 105 for operating the dose delivery actuator mechanism within the catheter handpiece and thereby delivering the desired dose. Toward lumen end 102, there is a dose carpule insertion aperture 106 with an aperture door 107, and a dose metering member 108 which is used to set the amount of dose desired to be injected into the patient when the catheter handpiece is activated. Next to dose metering member 108 are dose metering markings 109 to provide the operator with an indication of the amount of dose that will be injected at various settings of dose metering member 108.

Figure 7:
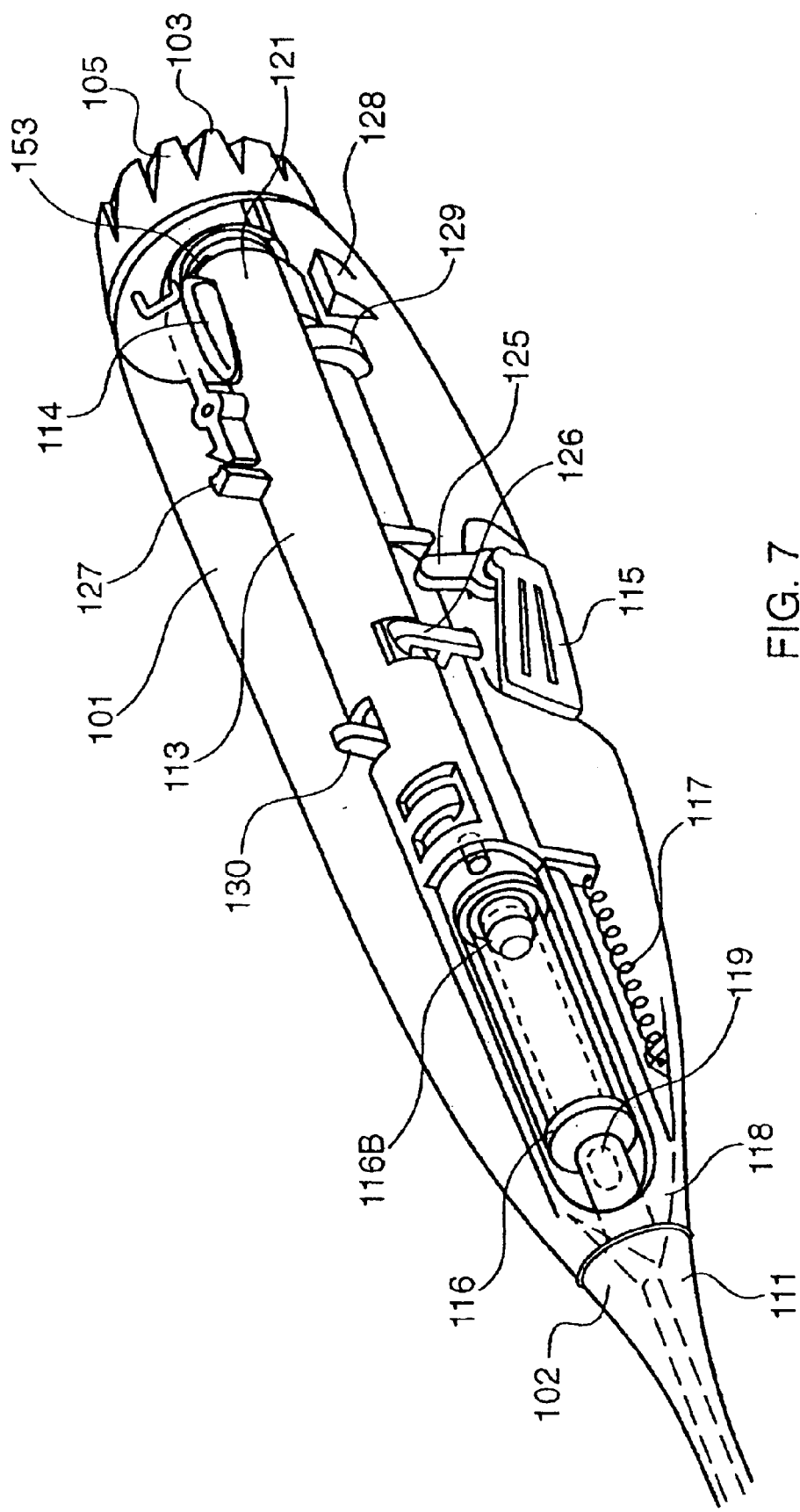
FIG. 7 is an oblique phantom view of a catheter handpiece and its carriage assembly in accordance with an second embodiment of the present invention.

FIG. 6 further shows a catheter affixed at its proximal end to the lumen end 102 of the handpiece, comprising an outer lumen 110 and a strain relief member 111. An inner lumen resides within outer lumen 110, and is affixed at its proximal end to a carriage assembly slidably located within handpiece housing 104 (inner lumen 112 and carriage assembly 113 are shown in FIG. 7 and discussed further, below). Once the catheter is properly positioned in the patient's body, carriage assembly release trigger 114 releases carriage assembly 113, which slides toward lumen end 102 of catheter handpiece 101 and thereby extends the distal end of inner lumen 112 and an injection needle tip at the end thereof (not shown) beyond the distal end of outer lumen 110 and into tissue at the desired dose injection site. Catheter handpiece 101 also contains a handpiece cocking lever 115, which moves carriage assembly 113 into its cocked position. Dose carpule 116 (shown in FIG. 7) is inserted into catheter handpiece 101 through aperture 106 and placed in carriage assembly 113 with carriage assembly 113 in the uncocked position.

Figure 8:
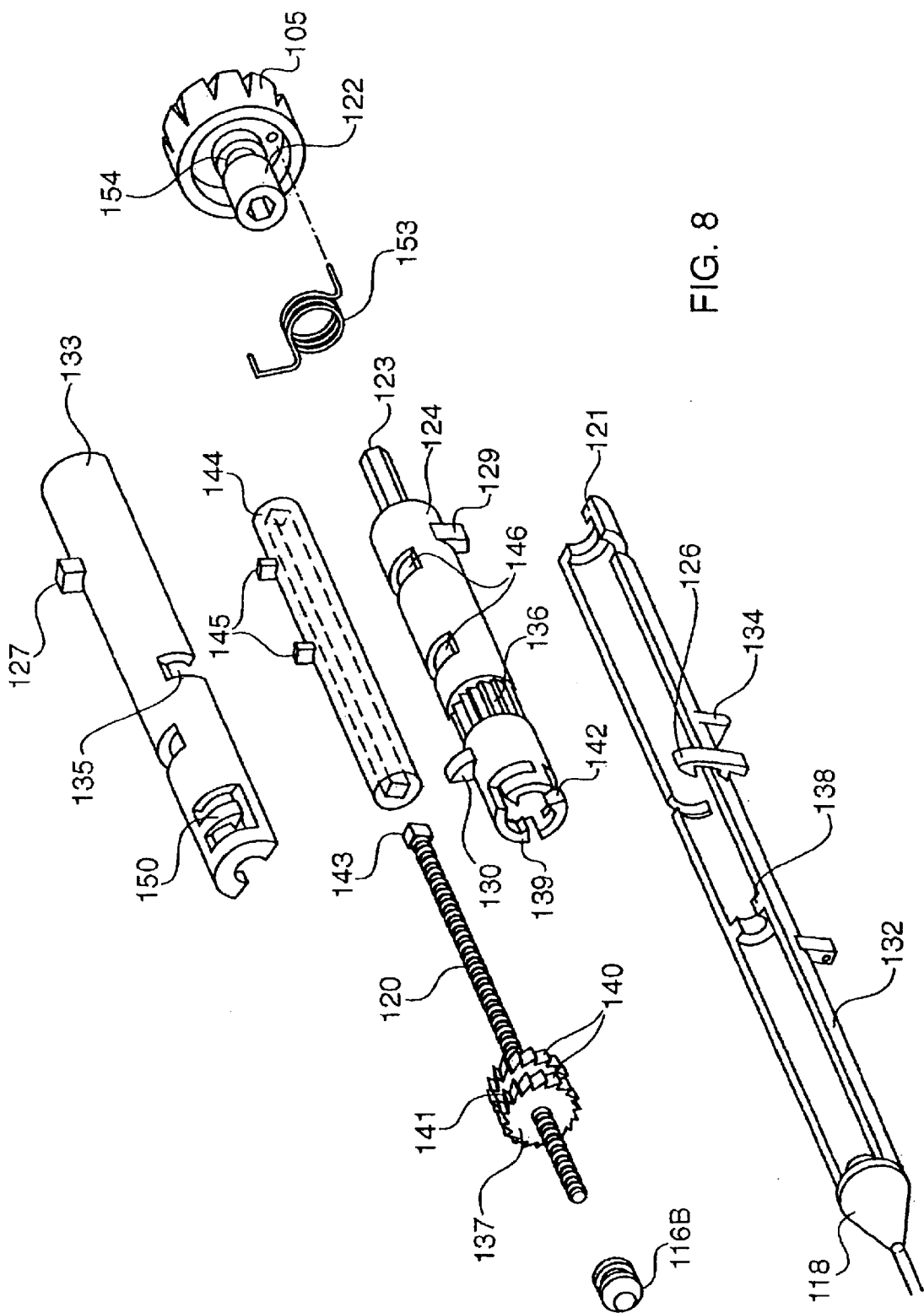
FIG. 8 is an exploded view of the carriage assembly in accordance with a second embodiment of the present invention.

Reference will now be made to FIG. 7 and FIG. 8 to highlight the principal differences in arrangement and operation of the second embodiment from the first embodiment (arrangements or operations which are similar between the two embodiments are not again described herein). FIG. 7 is an oblique phantom view of a catheter handpiece and its carriage assembly in accordance with the second embodiment of the present invention, while FIG. 8 is an exploded view of the carriage assembly of the second embodiment.

As shown in FIG. 7, carriage assembly 113 is slidably located within handpiece housing 104 such that carriage assembly 113 can slide between lumen end 102 and actuator end 103 of the catheter handpiece housing. A spring 117 is connected at one end to carriage assembly 113 and at its other end to handpiece housing 104, and biases carriage assembly 113 toward lumen end 102 of the catheter handpiece housing. At the carriage assembly's lumen end 118 there is a dose carpule receiving flange 119, to which the proximal end of inner lumen 112 is affixed. Outer lumen 110 is shown affixed via strain relief member 111 to lumen end 102 of handpiece housing 104.

As in the first embodiment, a dose delivery actuator rod 120 is located between dose carpule 116 and actuator end 121 of the carriage assembly. Dose delivery actuator rod 120 is positioned on carriage assembly 113 such that when actuated, the actuator moves toward dose carpule 116 and applies a force to carpule piston 116B that causes the medication therein to pass from dose carpule 116 through dose carpule receiving flange 119 and inner lumen 112 to reach the desired injection site within the patient's body.

Additional features shown in FIG. 7 include actuator knob 105 at actuator end 103 of handpiece housing 104. As shown in FIG. 8, actuator knob 105 has an internal projection 122 extending from its center toward carriage assembly 113, which contains an axial hexagonal hole. Actuator knob 105 is coupled to the catheter handpiece through the fitting of an axial hexagonal hole in projection 122 over a corresponding hexagonal end projection 123 of dose delivery actuator tube 124, and by trapping of a groove 154 in projection 122 between the halves of the handpiece body. Actuator knob 105 is returned to its rest position after use by a spiral spring 153 concentrically located over internal projection 122. One end of spring 153 engages a hole in the underside of actuator knob 105, while the other end of spring 153 engages a hole in handpiece housing 104 (shown in FIG. 7).

Returning to FIG. 7, also shown are a number of components whose operation will be described further, below, including handpiece cocking lever 115, which is pivotally mounted to handpiece housing 104, pushing arm 125 configured to pivot with handpiece cocking lever 115 and pushes carriage assembly 113 into its cocked position, actuator tube holdback ratchet lever 126, carriage release trigger 114, and carriage assembly tab 127, which is releasably captured by carriage release trigger 114 as the catheter handpiece is cocked. Within the inner surface of handpiece housing 104 toward its actuator end 103 is dose delivery blocking ridge 128, which cooperates with dose tube safety tab 129 when carriage assembly 113 is in its cocked position to prevent delivery of a dose from dose carpule 116 if inner lumen 112 has not been deployed. Finally, FIG. 7 shows dose tube stop tab 130 projecting outward through slot 131 in carriage assembly 113 from outside of actuator tube 124. Dose stop tube tab 130 interacts with dose metering steps on an inner surface of dose metering member 108 (not shown) to halt dose delivery when the desired amount of medication or other substance has been delivered to the desired injection location within the patient.

FIG. 8 shows an exploded view of carriage assembly actuator mechanism of the second embodiment. Carriage assembly 113 has a lower member 132 and upper member 133 between which the components of the dose delivery actuator mechanism reside. On the underside of carriage assembly member 132 is a carriage cocking bar 134. When handpiece cocking lever 115 is depressed, pushing arm 125 pivots, pushing carriage cocking bar 134 and carriage assembly 113 toward actuator end 103 of the catheter handpiece until carriage cocking tab 127 on carriage assembly member 133 is releasably captured by carriage release trigger 114 (shown in FIG. 7). At the beginning of the stroke of handpiece cocking lever 115, the initial motion of the lever results in contact with actuator tube holdback ratchet lever 126 (shown in FIG. 7), which is pivotally mounted on carriage assembly 113 such that its holdback pawl passes through slot 135 in carriage assembly 113 and engages actuator tube ratchet teeth 136, thereby preventing clockwise rotation of actuator tube 124. When handpiece cocking lever 115 contacts actuator tube holdback ratchet lever 126, the lever pivots and disengages actuator tube ratchet teeth 136, permitting the actuator tube to rotate clockwise to ensure it is in its starting position in the dose delivery process.

The following describes the arrangement of the dose delivery actuator in the second embodiment of the present invention. As in the first embodiment, dose delivery actuator rod 120 has external threads along its length which engage corresponding internal threads in a hole in the center of actuator nut 137. Actuator nut 137 rests against indexing surfaces 138 in the interior of carriage assembly members 132 and 133 (indexing surface within member 133 not shown) and the face 139 of actuator tube 124, such that actuator nut 137 is constrained from moving toward the lumen end 118 or actuator end 121 of the carriage assembly. As with the first embodiment, actuator nut 137 may only rotate about the longitudinal axis of dose delivery actuator 120, and actuator nut 137 and dose delivery actuator rod 120 cooperate to permit extension of actuator rod 120.

Actuator nut 137 further has ratchet teeth 140 formed on both sides of its outer circumference adjacent to circumferential groove 141. Actuator nut ratchet teeth 140 are releasably engaged, to one side of circumferential groove 141 by a hook 150 on carriage assembly member 133, and to the other side of the nut by corresponding ratchet hooks 142 within the face of lumen end of actuator tube 124. The actuator nut ratchet teeth 140 on both sides of circumferential band 141 are arranged in the same direction, such that when the ratchet hooks are engaged, actuator nut 137 cannot rotate in a clockwise direction viewed from the lumen end of the carriage assembly.

Dose delivery actuator rod 120 has at its actuator end a square-shaped head 143 which engages a corresponding recess within substantially the entire length of dose delivery actuator drive nut 144. Actuator drive nut 144 in turn rests concentrically within actuator tube 124. Along the exterior circumference of actuator drive nut 144 are drive nut holding tabs 145, which pass through slots 146 in actuator tube 124 and engage corresponding recesses in the interior surface of carriage assembly member 133 (not shown) to prevent rotation of drive nut 144 during operation of catheter handpiece 101.

Also shown in FIG. 8 is dose metering stop tab 130 extending radially from the outside circumference of actuator tube 124 through dose stop slot 131 in carriage assembly member 133. Dose metering stop tab 130 is positioned along actuator tube 124 such that when the dose delivery operation is performed, the dose stop tab contacts dose metering member 108 and stops further dose injection when the desired dose is reached.

Operation of the catheter handpiece of the second embodiment begins with the operator depressing handpiece cocking lever 113, which simultaneously causes carriage assembly 113 to slide toward the actuator end 103 of catheter handpiece 101 until carriage assembly tab 127 is captured and releasably held by carriage assembly release trigger 114, and causes actuator tube holdback lever 126 to pivot, thereby releasing actuator tube 124 to rotate clockwise by force of actuator knob spring 153 to return to its rest position and to permit dose tube safety tab 129 to engage dose delivery blocking ridge 128, thereby preventing dose delivery while the handpiece is cocked.

Following a physician's insertion of the catheter into the patient's body and maneuvering of the catheter to the desired injection site, the operator depresses carriage assembly release trigger 114, freeing carriage assembly 113 to slide toward lumen end 102 of catheter handpiece 101, thereby extending the injection needle tip on the distal end of inner lumen 112 into the desired injection site. The movement of carriage assembly 113 toward lumen end 102 also allows dose tube safety tab 129, which extends from actuator tube 124, to pass dose delivery blocking ridge 128 and thereby permit actuator tube 124 to subsequently rotate counter-clockwise when operated. In order to deliver the desired dose, actuator knob 105 is manually rotated counter-clockwise by the operator, which in turn rotates actuator tube 124 (to which actuator knob 105 is coupled by engagement of knob projection 122 with actuator tube 123) counter-clockwise until dose metering stop tab 130 projecting from the outer surface of actuator tube 124 reaches the inner surface of dose metering member 108. As in the first embodiment, the range of travel of the actuator tube 124 is relatively short (approximately 45 degrees), however, any length of arc less than a complete circle could be used as long as the length of dose stop slot 152 is not so great as to compromise the structural integrity of the carriage assembly.

The counter-clockwise rotation of actuator tube 124 causes actuator nut 137 (whose ratchet teeth 140 are engaged by ratchet hooks 142 on face 139 of actuator tube 124) to also rotate counter-clockwise with actuator tube 124. Due to the interaction of the internal threads of actuator nut 137 with the external threads on dose delivery actuator rod 120, actuator nut 137 drives dose delivery actuator rod 120 toward, and into contact with, dose carpule piston 116B. Dose delivery actuator rod 120 then presses on dose carpule piston 116B to begin forcing the contents of the carpule into dose carpule receiving flange 119 and thence through inner lumen 112 and the injection needle tip into the desired injection site. The counter-clockwise rotation of actuator nut 137 and axial motion of dose delivery actuator rod 120 continues until dose metering stop tab 130 reaches the step on inner surface of dose metering member 108 corresponding to the desired dose. When dose metering stop tab 130 reaches the selected dose stop step, the counter-clockwise rotation of actuator tube 124 and actuator nut 137 and the axial motion of dose delivery actuator rod 120 toward the lumen end of carriage assembly 113 are halted, completing the delivery of the desired dose.

Associated with the foregoing embodiment of the present invention is a method for delivery of a desired dose using the catheter handpiece of this embodiment. In order to deliver a desired dose of medication or other substance to a desired injection site within a patient's body, the catheter handpiece of the second embodiment is be prepared for use by placing a dose carpule containing the substance to be injected into the patient through carpule insertion aperture 106 and onto carriage assembly 113, and then closing aperture door 107. Next, in order to prime the inner lumen with the substance to be injected, a sequence of operating cocking lever 115, pressing carriage assembly release trigger 114 and rotating actuator advance knob 105 is performed as many times as necessary to cause the substance to be injected to reach the distal end of inner lumen 112.

Once the substance has reached the end of the inner lumen, the catheter handpiece may be re-cocked in the manner previously described and dose metering member 108 set to the desired dose, whereupon the physician may then insert the catheter, comprising outer lumen 110 and inner lumen 112, into the patient's body and maneuver the catheter to the desired injection site in the conventional manner. Once the catheter is located at the desired injection site, the catheter operator may depress carriage assembly release trigger 114 to cause carriage assembly 113 to slide forward and thus cause the distal end of inner lumen 112 to extend beyond outer lumen 110 into the desired injection site. Once inner lumen 112 has been deployed, the catheter operator may rotate actuator knob 105 counter-clockwise viewed from lumen end 102 until dose stop tab 130 on actuator tube 124 reaches the dose stop step on dose metering member 108 corresponding to the desired dose. Rotation of actuator knob 105 causes actuator tube 124 to rotate actuator nut 137 counter-clockwise, in turn causing dose delivery actuator rod 120 to extend forward to press on dose carpule piston 116B, and thereby cause the desired dose to pass from the dose carpule through dose carpule receiving flange 119 and inner lumen 112, and thence to the desired injection site within the patient's body. Following delivery of the desired dose, the physician may cock the catheter handpiece to withdraw the inner lumen tip into the outer lumen, and then may remove the catheter from the patient's body, or alternatively, if the contents of the dose carpule have not all been injected, and another dose may be delivered to a desired injection site.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A dose delivery device for delivering a desired dose to an injection site within a patient's body, comprising:
    a housing;
    an outer lumen, a proximal end of which is affixed to a lumen end of the housing;
    a carriage assembly, slidably located within the housing;
    an inner lumen, slidably located within the outer lumen, wherein a proximal end of the inner lumen is affixed to a lumen end of the carriage assembly, and a distal end of the inner lumen extends beyond a distal end of the outer lumen when the carriage assembly slides toward the lumen end of the housing;
    a dose delivery actuator;
    at least one cocking member for placing the carriage assembly and the dose delivery actuator into respective cocked conditions;
    a carriage assembly release trigger;
    a dose release trigger; and
    a dose metering member operable from outside the housing,
    wherein the carriage assembly when released from its cocked condition by the carriage assembly release trigger is biased to slide toward the lumen end of the housing, the dose delivery actuator when released from its cocked condition by the dose release trigger is biased to apply a force to a dose carpule placed on the carriage assembly to cause the desired dose to pass from the dose carpule through the inner lumen, and dose delivery actuator movement is halted by the dose metering member when the desired dose has been delivered.

2. The dose delivery device of claim 1 wherein an inner lumen extension spring biases the carriage assembly toward the lumen end of the housing.

3. The dose delivery device of claim 2, wherein the dose delivery actuator is located at an actuator end of the carriage assembly opposite the lumen end.

4. The dose delivery device of claim 3, wherein the dose delivery actuator includes a dose delivery actuator rod and an actuator spring which biases the dose delivery actuator rod toward the dose carpule.

5. The dose delivery actuator of claim 4, wherein
    the carriage assembly includes at its lumen end a dose carpule receiving flange in communication with the proximal end of the inner lumen,
    the dose carpule receiving flange and a lumen end of the dose delivery actuator are separated by a distance sufficient to accommodate the dose carpule, and
    when the dose delivery actuator rod presses on the dose carpule, the desired dose passes from the dose carpule though the dose carpule receiving flange into the inner lumen.

6. The dose delivery device of claim 5, wherein the dose delivery actuator further comprises:
    an actuator drive nut, including
        a longitudinal recess configured to receive the dose delivery actuator rod and preclude rotation of the actuator rod relative to the drive nut, and
        a tab extending radially from the actuator drive nut and engaging the carriage assembly to preclude rotation of the actuator drive nut relative to the carriage assembly;
    an actuator tube, including
        a dose stop tab which cooperates with the dose metering member to halt actuator tube rotation, and
        at least one ratchet pawl located at a lumen end of the actuator tube; and
    an actuator nut, located adjacent to the lumen end of the actuator tube, including
        a plurality of ratchet teeth on an external circumferential surface, and
        an internally-threaded axial hole which cooperates with external threads on the dose delivery actuator rod,
    wherein
    the actuator drive nut is located within the actuator tube, the actuator spring is concentrically located therebetween, and the actuator tube engages a first actuator spring end and the actuator drive nut engages a second actuator spring end,
    a first portion of the actuator nut ratchet teeth are engaged by a ratchet pawl on the carriage assembly such that the actuator nut is prevented from rotating with the actuator tube during dose delivery actuator cocking, and
    a second portion of the actuator nut ratchet teeth are engaged by the ratchet pawl at a lumen end of the actuator tube such that when the actuator tube rotates under the bias of the actuator spring, the actuator nut rotates with the actuator tube and causes the dose delivery actuator to advance against the dose carpule until actuator tube rotation is halted by the dose metering member.

7. The dose deliver device of claim 6, wherein the cocking member is an actuator knob located at the actuator/end of the housing, wherein the actuator knob rotates about a longitudinal axis of the carriage assembly.

8. The dose delivery device of claim 7, wherein the actuator knob further comprises:
    a knob body;
    a cylindrical projection on an underside of the knob body toward the lumen end of the housing, wherein the inner diameter of the cylindrical projection is larger than an outer diameter of the actuator end of the carriage assembly,
    an actuator knob return spring, wherein a first knob spring end is connected to the actuator knob and a second knob spring end is connected to the housing, wherein the actuator knob returns to a starting position when released; and
    at least one inner flange located on an interior surface of the cylindrical projection, wherein the inner flange cooperated with a corresponding helical flange on the outer surface of the carriage assembly;
    at least one actuator knob engagement surface which cooperates with a corresponding cocking flange on the dose delivery actuator tube, wherein
    when the actuator knob is rotated, the at least one actuator knob engagement surface rotates the actuator tube into a cocked position, and the at least one inner flange moves the carriage assembly toward the actuator end of the housing to place the carriage assembly in its cocked condition.

9. The dose delivery device of claim 5, wherein the housing includes a dose carpule insertion aperture adjacent to the dose carpule receiving flange, the device further comprising:
   a dose carpule insertion aperture cover; and
   a dose carpule pressing block,
   wherein the dose carpule pressing block is configured to cooperate with aperture cover and the carriage assembly such that when the aperture cover is closed, the dose carpule pressing block presses the dose carpule against the dose carpule receiving flange.

10. A method for delivery of a desired dose to an injection site within a body of a patient using the dose delivery apparatus claim 1, comprising the steps of
   placing a dose carpule containing a substance to be injected into the patient's body onto the carriage assembly;
   setting the desired dose with the dose metering member;
   priming the inner lumen with the substance to be injected;
   placing the carriage assembly and the dose delivery actuator into their respective cocked conditions;
   inserting the outer lumen into the patient's body and maneuvering the outer lumen to the desired injection site;
   releasing the carriage assembly to extend the distal end of the inner lumen into the desired injection site;
   releasing the dose delivery actuator to cause the desired dose to pass from the dose carpule through the inner lumen to the desired injection site;
   withdrawing the outer lumen from the patient's body.

11. The method of claim 10, wherein before the step of withdrawing the catheter from the patient's body, the method further comprises the steps of:
   placing the carriage assembly and the dose delivery actuator into their respective cocked conditions;
   releasing the carriage assembly; and
   releasing the dose delivery actuator.

12. The method of claim 11, wherein after the step of placing the carriage assembly and the dose delivery actuator into their respective cocked conditions, the method further comprises the step of:
   repositioning the outer lumen to a different desired injection site.

13. The method of claim 11, wherein between the steps of placing the carriage assembly and the dose delivery actuator into their respective cocked conditions and releasing the dose delivery actuator, the method further comprises the step of:
   resetting the dose metering member to a new desired dose.

14. A dose delivery device for delivering a desired dose to an injection site within a body of a patient, comprising:
   a housing;
   an outer lumen, a proximal end of which is affixed to a lumen end of the housing;
   a carriage assembly, slidably located within the housing;
   an inner lumen, slidably located within the outer lumen, wherein a proximal end of the inner lumen is affixed to a lumen end of the carriage assembly, and a distal end of the inner lumen extends beyond a distal end of the outer lumen when the carriage assembly slides toward the lumen end of the housing;
   a dose delivery actuator;
   at least one cocking member for placing the carriage assembly into a cocked condition and the dose delivery actuator into a starting condition;
   a carriage assembly release trigger;
   a dose release actuator; and
   a dose metering member operable from outside the housing,
   wherein the carriage assembly when released from its cocked condition by the carriage assembly release trigger is biased to slide toward the lumen end of the housing, the dose delivery actuator when moved from its starting condition by the dose release actuator is biased to apply a force to a dose carpule placed on the carriage assembly to cause the desired dose to pass from the dose carpule through the inner lumen, and dose delivery actuator movement is halted by the dose metering member when the desired dose has been delivered.

15. The dose delivery device of claim 14 wherein an inner lumen extension spring biases the carriage assembly toward the lumen end of the housing.

16. The dose delivery device of claim 15, wherein the dose delivery actuator is located at an actuator end of the carriage assembly opposite the lumen end.

17. The dose delivery device of claim 16, wherein the dose delivery actuator includes a dose delivery actuator rod which advances toward the dose carpule when the dose release actuator is operated.

18. The dose delivery actuator of claim 17, wherein
   the carriage assembly includes at its lumen end a dose carpule receiving flange in communication with the proximal end of the inner lumen,
   the dose carpule receiving flange and a lumen end of the dose delivery actuator are separated by a distance sufficient to accommodate the dose carpule, and
   when the dose delivery actuator rod presses on the dose carpule, the desired dose passes from the dose carpule though the dose carpule receiving flange into the inner lumen.

19. The dose delivery device of claim 18, wherein the dose delivery actuator further comprises:
   an actuator drive nut, including
      a longitudinal recess configured to receive the dose delivery actuator rod and preclude rotation of the actuator rod relative to the drive nut, and
      a tab extending radially from the actuator drive nut and engaging the carriage assembly to preclude rotation of the actuator drive nut relative to the carriage assembly;
   an actuator tube, including
      a dose stop tab which cooperates with the dose metering member to halt actuator tube rotation, and
      at least one ratchet pawl located at a lumen end of the actuator tube; and
   an actuator nut, located adjacent to the lumen end of the actuator tube, including
      a plurality of ratchet teeth on an external circumferential surface, and
      an internally-threaded axial hole which cooperates with external threads on the dose delivery actuator rod,
   wherein
   the actuator drive nut is concentrically located within the actuator tube,
   the actuator tube cooperates with the dose release actuator to transfer the motion of the dose release actuator to the dose delivery actuator rod, a first portion of the actuator nut ratchet teeth are engaged by a ratchet pawl on the carriage assembly such that the actuator nut is prevented from rotating with the actuator tube during dose delivery actuator cocking, and a second portion of the actuator nut ratchet teeth are engaged by the ratchet pawl at a lumen end of the actuator tube such that when the actuator tube rotates under in response to operation of the dose release actuator, the actuator nut rotates with the actuator tube and causes the dose delivery actuator to advance against the dose carpule until actuator tube rotation is halted by the dose metering member.

20. The dose delivery device of claim 19, wherein the dose release actuator is a knob located at the actuator end of the housing, the actuator knob comprising:

an knob body; and a projection from an underside of the knob body toward the lumen end of the housing, wherein at least one actuator tube engagement surface cooperates with a corresponding surface of the projection such that rotation of the actuator knob rotates the actuator tube.

21. The dose delivery device of claim 20, wherein the actuator tube engagement surface is an extension from an actuator end of the actuator tube and has a polygonal cross-section which cooperates with a corresponding polygonal cross-section axial recess in the actuator knob projection.

22. The dose delivery device of claim 21, wherein the cocking member is a lever pivotally mounted on the housing alongside the carriage assembly and configured to cause an actuator tube holdback lever to release the actuator tube to permit movement of the actuator tube to a starting position, and to push the carriage assembly toward the actuator end of the housing until the carriage assembly reaches a cocked position.

23. A method for delivery of a desired dose to an injection site within a body of a patient using the dose delivery apparatus claim 14, comprising the steps of placing a dose carpule containing a substance to be injected into the patient's body onto the carriage assembly;

setting the desired dose with the dose metering member;

priming the inner lumen with the substance to be injected;

placing the carriage assembly and the dose delivery actuator into their respective cocked and starting conditions;

inserting the outer lumen into the patient's body and maneuvering the outer lumen to the desired injection site;

releasing the carriage assembly to extend the distal end of the inner lumen into the desired injection site;

operating the dose delivery actuator to cause the desired dose to pass from the dose carpule through the inner lumen to the desired injection site;

withdrawing the outer lumen from the patient's body.

24. The method of claim 23, wherein before the step of withdrawing the catheter from the patient's body, the method further comprises the steps of:

placing the carriage assembly and the dose delivery actuator into their respective cocked and starting conditions;

releasing the carriage assembly; and operating the dose delivery actuator.

25. The method of claim 24, wherein after the step of placing the carriage assembly and the dose delivery actuator into their respective cocked and starting conditions, the method further comprises the step of:

repositioning the outer lumen to a different desired injection site.

26. The method of claim 24, wherein between the steps of placing the carriage assembly and the dose delivery actuator into their respective cocked and starting conditions and operating the dose delivery actuator, the method further comprises the step of:

resetting the dose metering member to a new desired dose.

* * * * *